| United States Patent [19] | [11] Patent Number: 4,868,168 |
| --- | --- |
| O'Laughlin et al. | [45] Date of Patent: Sep. 19, 1989 |

[54] STEROID OINTMENT FORMULATION

[75] Inventors: Richard L. O'Laughlin, North Brunswick; Andrea Panaggio, Jamesburg; Sailesh A. Varia, Plainsboro, all of N.J.

[73] Assignee: E. R. Squibb & Sons, Inc., Princeton, N.J.

[21] Appl. No.: 120,276

[22] Filed: Nov. 13, 1987

[51] Int. Cl.$^4$ ............................................. A61K 31/56
[52] U.S. Cl. .................... 514/179; 514/177; 514/178; 514/180
[58] Field of Search ............ 514/169, 170–179, 514/180–182, 937–941, 943, 944, 947, 969, 970, 973

[56] References Cited

U.S. PATENT DOCUMENTS

| 2,801,202 | 7/1957 | Poetsch | 514/171 |
| 3,856,954 | 12/1974 | Jackson | 514/174 |
| 4,048,310 | 9/1977 | Chen et al. | 514/171 |
| 4,233,295 | 11/1980 | Hill et al. | 424/238 |
| 4,361,559 | 11/1982 | Varma | 424/243 |

FOREIGN PATENT DOCUMENTS 0069423 1/1983 European Pat. Off. ............ 514/179

Primary Examiner—H. M. S. Sneed
Assistant Examiner—J. Saba
Attorney, Agent, or Firm—Burton Rodney

[57] ABSTRACT

A steroid ointment formulation which has enhanced physical and chemical stability is formed of 11$\beta$,17$\alpha$)-17-(ethylthio)-9$\alpha$-fluoro-11$\beta$-hydroxy-17-(methylthio)androsta-1,4-dien-3-one (tipredane), and a vehicle containing as major ingredients propylene glycol and water, cetearyl alcohol and ceteareth 20 or other dispersing agent for propylene glycol, together with a sodium or potassium citrate and magnesium hydroxide buffer to impart a neutral or slightly alkaline apparent pH (5 to 9), a non-acidic long chain fatty acid wax to impart proper consistency to the ointment and sodium metabisulfite and butylated hydroxy toluene as antioxidants, together with thickeners, emollients, lubricants and other conventional ointment formulation ingredients.

12 Claims, No Drawings

STEROID OINTMENT FORMULATION

FIELD OF THE INVENTION

The present invention relates to a steroid ointment formulation which is cosmetically elegant and has enhanced physical and chemical stability and contains (11β,17α)-17-(ethylthio)-9α-fluoro-11β-hydroxy-17-(methylthio)androsta-1,4-di ®n-3-one (tipredane) as the active ingredient.

BACKGROUND OF THE INVENTION

U.S. Pat. No. 4,361,559 to Varma discloses antiinflammatory 17,17-bis(substituted thio)androstenes of the formula

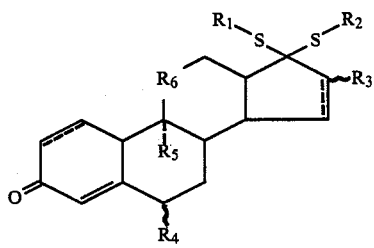

wherein $R_1$ and $R_2$ are the same or different and each is alkyl, cycloalkyl or aryl;

$R_3$ is hydrogen, hydroxy, alkoxy, aryloxy, alkylthio, arylthio,

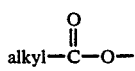

or halogen;

$R_4$ is hydrogen, methyl, hydroxy,

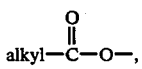

or halogen;

$R_5$ is hydrogen or halogen; and $R_6$ is carbonyl or β-hydroxymethylene. A broken line in the 1,2-, 6,7- and 15,16-position of a structural formula indicates the optional presence of ethylenic unsaturation.

Included among the compounds covered in the Varma patent is tipredane which has been found to be a highly effective topical antiinflammatory agent.

Tipredane is practically insoluble in water (less than 0.0002 mg/ml at 25° C.); 1:1 hydroalcoholic mixtures of tipredane are unstable under acidic conditions. Further, tipredane itself is susceptible to oxidation. It has been found that propylene glycol is an excellent solubilizer for tipredane and a good preservative. However, where it has been attempted to formulate a tipredane ointment containing propylene glycol and an ointment base such as Plastibase (mineral oil gelled with polyethylene) or petrolatum, it has been found that when propylene glycol is dispersed in Plastibase or petrolatum, the propylene glycol coalesces and separates out of the Plastibase or petrolatum.

Until now, attempts to prepare a stable ointment formulation containing tipredane which overcomes the above formulation problems have not been successful.

DESCRIPTION OF THE INVENTION

In accordance with the present invention, a topical steroid ointment formulation is provided which is in the form of a cosmetically elegant wax-gel type ointment, which contains the steroid tipredane as its active ingredient and has excellent physical and chemical stability. The ointment formulation according to the present invention contains in addition to tipredane, an ointment base in the form of an emollient wax-gel, which is free of petrolatum and Plastibase and contains one or more oil emollients, water as a solubilizer for salts (such as sodium citrate and sodium metabisulfite), propylene glycol as a preservative and a solubilizer for tipredane, a dispersing agent for propylene glycol which will inhibit coalescence of the propylene glycol, such as cetearyl alcohol and ceteareth-20 (preferably 3:1) which also may serve as a thickener, one or more thickeners, such as a non-acidic long chain fatty acid wax, one or more pH adjusters to impart a neutral or slightly alkaline apparent pH of 5 to 9 to the ointment, one or more antioxidants and optionally one or more lubricants.

The tipredane steroid will be employed in the form of a micronized powder having an average particle size of less than about 75 microns and will be present in an amount within the range of from about 0.005 to about 0.5% by weight and preferably from about 0.05 to about 0.3% by weight based on the total weight of the tipredane ointment formulation.

The ointment base is in the form of a wax-gel having emollient, occlusive and hydrophilic properties. The ointment base includes a dispersed hydrophilic phase which contains water and propylene glycol which act as a solubilizer for a portion of the tipredane as well as for pH buffer (such as sodium citrate) and antioxidant such as sodium metabisulfite. Thus, the hydrophilic phase will contain propylene glycol in an amount within the range of from about 3 to about 25% by weight and preferably from about 5 to about 20% by weight of the tipredane ointment formulation. Water, a solubilizer for salts, is present in an amount within the range of from about 0.1 to about 15% and preferably from about 0.2 to about 10% by weight of the tipredane ointment formulation.

The emollients which are present in the ointment base to impart cosmetic elegance including a smooth and soothing feel thereto will be present in an amount within the range of from about 25 to about 85% and preferably from about 35 to about 75% by weight of the tipredane ointment formulation. Examples of emollients suitable for use herein include but are not limited to mineral oil, preferably heavy mineral oil, polysynlane oil (that is hydrogenated polyisobutene), lanolin alcohol, a mixture of mineral oil and lanolin alcohol (9:1) as sold under the trademark Amerchol L-101 (Amerchol Corp., a unit of CPC International), cetyl alcohol, isopropyl isostearate, isopropyl myristate, isopropyl palmitate or octyl dodecyl stearate. Preferred are heavy mineral oil, polysynlane oil and mixtures thereof (2:1 to 0.5:1).

The dispersing agent for propylene glycol will be present in an amount within the range of from about 1 to about 15% and preferably from about 2 to about 10% by weight of the tipredane ointment formulation. The preferred dispersing agent for the propylene glycol will be a mixture of cetearyl alcohol and ceteareth-20 in a ratio to each other of within the range of from about 5:1 to about 1:1 and preferably from about 4:1 to about 2:1. A preferred such mixture is available under the name Promulgen D (a trademark of Robinson-Wagner) which is a 75%-25% mixture of cetearyl alcohol and ceteareth-20. Cetearyl alcohol is defined as a mixture of fatty alcohols predominantly formed of cetyl and stearyl alcohols. Ceteareth-20 is the polyethylene glycol ether of cetearyl alcohol that conforms generally to the formula $$R(OCH_2CH_2)_nOH$$

where R represents a blend of cetyl and stearyl radicals and n has an average value of 20. Other examples of propylene glycol dispersants suitable for use herein include, but are not limited to polysorbate 20, polysorbate 60, polysorbate 65 or polysorbate 80 (polysorbate representing polyoxyethylene sorbitan monostearate).

An important feature of the ointment formulation of the invention is its excellent chemical stability and physical stability. This is achieved in part by controlling the apparent pH of the ointment by including a buffer in an amount to impart a neutral or slightly alkaline apparent pH of 5 to 9 to the ointment. Examples of buffers suitable for use herein include but are not limited to sodium citrate, potassium citrate, magnesium hydroxide, an alkali metal hydroxide such as sodium hydroxide or potassium hydroxide, or aluminum hydroxide.

The ointment formulation of the invention will include one or more antioxidants such as sodium metabisulfite, butylated hydroxytoluene, butylated hydroxyanisole, propyl gallate or sodium ascorbate in an amount within the range of from about 0.01 to about 1% and preferably from about 0.02 to about 0.5% by weight of the tipredane ointment formulation. Preferred are a combination of sodium metabisulfite and butylated hydroxy toluene (4:1 to 0.25:1).

Thickeners will be present in an amount within the range of from about 5 to about 20% and preferably from about 7 to about 17% by weight of the tipredane ointment formulation.

Examples of thickeners suitable for use herein include but are not limited to non-acidic long chain fatty acid waxes, such as $C_{18}$-$C_{36}$ acid triglyceride (available as Syncrowax HGLC, trademark of Croda), white wax, carnauba wax, paraffin wax or ceresin wax. The cetearyl alcohol-ceteareth 20 (Promulgen Type D) may also serve as a thickener. Preferred is a mixture of the Syncrowax HGLC, and cetearyl alcohol and ceteareth 20 (3:1 to 0.3:1).

In addition, the ointment formulation of the invention will include a lubricant or defoamer in an amount within the range of from about 0.5 to about 6% and preferably from about 1.5 to about 5% by weight of the tipredane ointment formulation. Examples of lubricants or defoaming agents suitable for use herein include but are not limited to silicones such as dimethicone (Silicone DC 200 fluid [350 CS]), polyphenylmethylsiloxane or polydimethylsiloxane.

The following represents preferred ointment formulations in accordance with the present invention.

| Ingredient | Range Percent w/w | | |
|---|---|---|---|
| Tipredane (in form of micronized powder) (<75μ) | 0.05 | to | 0.3 |
| Water | 0.2 | to | 10 |
| Propylene glycol | 5 | to | 20 |
| Sodium citrate | 0.01 | to | 0.1 |
| Magnesium hydroxide (hydrate) | 0.1 | to | 1 |
| Sodium metabisulfite | 0.005 | to | 0.05 |
| Butylated hydroxytoluene | 0.02 | to | 0.5 |
| Silicone DC 200 fluid | 1.5 | to | 5 |
| Polysynlane oil (hydrogenated polyisobutene) | 20 | to | 40 |
| Mineral oil | 25 | to | 45 |
| Cetearyl alcohol (and) ceteareth 20 (3:1) | 2 | to | 10 |
| Syncrowax HGLC ($C_{18}$—$C_{36}$ acid triglyceride) | 7 | to | 17 |

The tipredane ointment formulations of the invention may be prepared as described in the working Examples and as outlined below.

Emollient such as polysynlane oil, and heavy mineral oil, antioxidant such as butylated hydroxytoluene and dispersing agent such as cetearyl alcohol (and) ceteareth 20 and Syncrowax HGLC and pH adjuster such as magnesium hydroxide are mixed using a suitable homogenizer. The batch is heated to 75°–80° C. and maintained at this temperature 30 minutes. The batch is then cooled to 70°–75° C. and silicone DC fluid (350 Centistokes) added. The batch (r to as the main batch) is cooled to 65°–70° C., with continuous homogenization.

To a separate suitable container, purified water USP, sodium citrate (pH adjuster) and antioxidant such as sodium metabisulfite are added while mixing after each addition. This aqueous solution is added to another vessel containing propylene glycol and the mix is mixed until uniform. After the main batch has attained 65°–70° C., the aqueous propylene glycol solution is added. Homogenization is maintained and the mix is cooled to 55°–57° C. and thereafter with continuous agitation is cooled to 46°–48° C.

The tipredane is slurried in an emollient such as mineral oil heavy. The slurry is milled and the mill is rinsed with mineral oil heavy. The tipredane is added with mixing to the main batch which is at 46°–48° C. The batch is cooled to 40° to 45° C. When the ointment begins to congeal, the batch is allowed to stand for 15–20 minutes followed by 1–2 minute slow mixing periods until the batch reaches 38°–39° C. The batch is allowed to stand overnight without agitation but with continued cooling.

The following Example represents a preferred embodiment of the present invention otherwise indicated, all temperatures are expressed in degrees Centigrade.

EXAMPLE

A 0.1% w/w tipredane wax-gel type ointment formulation having the following composition was prepared as described below.

| Ingredient | mg/gram |
|---|---|
| Tipredane, micronized (less than 75 microns) | 1 |
| Polysynlane oil (emollient) | 300 |
| Mineral oil, heavy (emollient) q.s. ca | 385.3 |
| Butylated hydroxytoluene (antioxidant) | 0.5 |
| Cetearyl alcohol (and) | 50 |

-continued

| Ingredient | mg/gram |
| --- | --- |
| ceteareth 20 (3:1) (dispersing agent and thickener) | 120 |
| Syncrowax HGLC (thickener) | |
| Magnesium hydrate (Marinco H-1211) (pH adjuster) | 2.5 |
| Silicone DC #200 fluid (350 centistokes) (lubricant and defoamer) | 30 |
| Water, purified USP (solubilizer) | 5 |
| Sodium citrate, powdered USP (pH adjuster) | 0.5 |
| Sodium metabisulfite NF (antioxidant) | 0.2 |
| Propylene glycol USP (solubilizer, preservative) | 105 |
| Total | 1000 |

To a clean, dry tared 340 qt. Glen bowl, polysynlane oil, mineral oil heavy, butylated hydroxytoluene, cetearyl alcohol (and) ceteareth 20 and Syncrowax HGLC were added.

To a separate suitable container, polysynlane oil and magnesium hydrate (Marinco H-1211) were added and allowed to settle. Using an Arde Barinco homogenizer, the mix was blended (avoid air entrapment) for 10–15 minutes. This mixture was transferred to the Glen bowl.

While mixing using a suitable homogenizer, the batch was heated to 75°–80° C. and maintained at this temperature for 30 minutes. The batch was cooled to 70°–75° C. and silicone DC #200 fluid (350 Centistokes) added. The batch was cooled to 65°–70° C., with continuous homogenization.

To a separate suitable container, purified water USP, sodium citrate powdered USP and sodium metabisulfite NF were added with mixing after each addition with a stainless steel spatula until dissolved. This aqueous solution was added to another stainless steel vessel containing propylene glycol and the mix was mixed uniform and covered. After the main batch attained 65°–70° C., the aqueous propylene glycol solution was added. Homogenization was maintained and the batch was cooled to 55°–57° C. The homogenizer was replaced with a Glen bowl mixer and with continuous agitation the batch was cooled to 46°–48° C.

In a suitable stainless steel container, the tipredane was slurried in mineral oil heavy. The slurry was milled into another stainless steel container and the mill rinsed with mineral oil heavy, adding the rinse to the slurry. When the main batch was at 46°–48° C., with continuous mixing, the tipredane slurry was added to the main batch. The bowl was scraped periodically to ensure homogeneous mixing. With continuous mixing, the batch was cooled to 43° C. When the ointment began to congeal, the batch was allowed to stand for 15–20 minutes followed by 1–2 minute slow mixing periods until the batch reached 38°–39° C. The batch was covered and allowed to stand overnight without agitation but with continued cooling. The next day, the batch was mixed for 2 minutes and the batch temperature determined. If the batch did not reached 23°–28° C., intermittent standing and slow mixing were begun until room temperature was achieved. Using a Moyno (or equivalent) pump equipped with an in-line 50 or 60 mesh stainless steel or nylon screen, the batch was transferred to a clean, tared ointment can.

The resulting tipredane ointment was found to have good chemical and physical stability even after prolonged storage at 5° C., room temperature and 40° C.

What is claimed is:

1. A tipredane ointment formulation having enhanced chemical and physical stability comprising tipredane in an amount within the range of from about 0.005 to about 0.5, and an ointment base in the form of an emollient wax-gel comprising one or more solubilizers for tipredane including propylene glycol in an amount within the range of from about 3 to about 25% water in an amount within the range of from about 0.1 to about 15%, one or more dispersing agents for dispersing propylene glycol which includes cetearyl alcohol, ceteareth 20 or a mixture thereof in an amount within the range of from about 1 to about 15%, at least one buffer to impart a neutral or slightly alkaline apparent pH to the ointment formulation, one or more emollients in an amount within the range of from about 25 to about 85%, one or more thickeners in an amount within the range of from about 5 to about 20%, optionally one or more lubricants in an amount within the range of from about 0.5 to about 6% and optionally one or more antioxidants in an amount within the range of from about 0.01 to about 1%, all of the above % being based on the weight of the tipredane ointment formulation, said ointment formulation being free of petroleum and mineral oil gelled with polyethylene.

2. The ointment formulation as defined in claim 1 wherein the solubilizer for tipredane is propylene glycol.

3. The ointment formulation as defined in claim 1 wherein the buffer is sodium citrate, potassium citrate, magnesium hydroxide, an alkali metal hydroxide, aluminum hydroxide or mixtures thereof.

4. The ointment formulation as defined in claim 1 wherein the thickener is a non-acidic long chain fatty acid wax.

5. The ointment formulation as defined in claim 1 further including one or more emollients, one or more lubricants and one or more antioxidants.

6. The ointment formulation as defined in claim 5 wherein the emollient is a mixture of polysynlane oil and mineral oil or mixtures thereof or cetyl alcohol, isopropyl isostearate, isopropyl myristate, isopropyl palmitate, or octyl dodecyl stearate; the lubricant is a silicone; and the antioxidant is sodium metabisulfite, butylated hydroxytoluene, butylated hydroxyanisole, propyl gallate or sodium ascorbate.

7. The ointment formulation as defined in claim 1 wherein the dispersing agent for propylene glycol is present in an amount within the range of from about 2 to about 10% by weight of the total ointment formulation and is a mixture of cetearyl alcohol and ceteareth-20.

8. The ointment formulation as defined in claim 4 wherein the non-acidic long chain fatty acid is present in an amount within the range of from about 7 to about 17% by weight and is $C_{18}$-$C_{36}$ acid triglyceride.

9. The ointment formulation as defined in claim 1 wherein the tipredane is present in an amount within the range of from about 0.05 to about 0.3% by weight, the solubilizer for tipredane is propylene glycol which is present in an amount within the range of from about 5 to about 20% by weight and water which is a solubilizer for salts is present in an amount within the range of from about 0.2 to about 10% by weight, all of the above % being based on the total weight of the ointment formulation.

10. The ointment formulation as defined in claim 1 wherein the buffer is sodium citrate or potassium citrate and magnesium hydroxide and is present in an amount to impart an apparatus pH of 5 to 9 to the ointment formulation.

11. The ointment formulation as defined in claim 5 wherein the emollients are present in an amount within range of from about 35 to about 75 weight %, the lubricant is present in an amount within the range of from about 1.5 to about 5% by weight and the anioxidant is present in an amount within the range of from about 0.02 to about 0.5% by weight.

12. The ointment formulation as defined in claim 1 having the formula

|  | % w/w |
|---|---|
| Tipredane, micronized | 0.1 |
| Polysynlane oil | 30 |
| Mineral oil, heavy q.s. ca | 38.5 |
| Butylated hydroxytoluene (preservative) | 0.05 |
| Cetearyl alcohol (and) ceteareth 20 | 5 |
| Syncrowax HGLC | 12 |
| Magnesium hydrate | 0.25 |
| Silicone DC #200 fluid (350 centistokes) | 3 |
| Water, purified USP | 0.5 |
| Sodium citrate, powdered USP | 0.05 |
| Sodium metabisulfite NF | 0.02 |
| Propylene glycol USP | 10.5 |

\* \* \* \* \*